(12) United States Patent
Castelli et al.

(10) Patent No.: US 7,569,729 B2
(45) Date of Patent: Aug. 4, 2009

(54) STABLE ATOMOXETINE HYDROCHLORIDE, A PROCESS FOR THE PREPARATION THEREOF, AND AN ANALYTICAL CONTROL OF ITS STABILITY

(75) Inventors: Eugenio Castelli, Arlate di Calco (IT); Paolo Riva, Monza (IT)

(73) Assignee: Teva Pharmaceutical Fine Chemicals S.R.L., Bulciago (LC) (IT)

( * ) Notice: Subject to any disclaimer, the term of this patent is extended or adjusted under 35 U.S.C. 154(b) by 63 days.

(21) Appl. No.: 11/399,055

(22) Filed: Apr. 5, 2006

(65) Prior Publication Data

US 2006/0252836 A1 Nov. 9, 2006

Related U.S. Application Data

(60) Provisional application No. 60/668,741, filed on Apr. 5, 2005, provisional application No. 60/686,386, filed on May 31, 2005, provisional application No. 60/688,406, filed on Jun. 7, 2005.

(51) Int. Cl.
*C07C 213/10* (2006.01)
*C07C 211/27* (2006.01)
*A61K 31/135* (2006.01)

(52) U.S. Cl. ..................... 564/347; 514/651

(58) Field of Classification Search .............. None
See application file for complete search history.

(56) References Cited

U.S. PATENT DOCUMENTS

| | | | |
|---|---|---|---|
| 4,018,895 A * | 4/1977 | Molloy et al. | |
| 4,777,291 A * | 10/1988 | Misner | |
| 4,868,344 A * | 9/1989 | Brown | |
| 5,658,590 A * | 8/1997 | Heiligenstein et al. | |
| 6,333,198 B1 * | 12/2001 | Edmeades et al. | |
| 6,541,668 B1 * | 4/2003 | Kjell et al. | |

FOREIGN PATENT DOCUMENTS

| | | | |
|---|---|---|---|
| DE | 41 23 253 A1 * | 1/1993 | |
| EP | 0 052 492 A1 * | 5/1982 | |
| EP | 0 193 405 A1 * | 9/1986 | |
| EP | 0 721 777 A2 * | 1/1995 | |
| EP | 1 798 215 A1 | 6/2007 | |
| WO | WO 94/00416 * | 1/1994 | |
| WO | WO 00/58262 * | 10/2000 | |
| WO | WO 00/64855 * | 11/2000 | |
| WO | WO 2006/004923 A2 * | 1/2006 | |
| WO | WO 2006/004976 A2 * | 1/2006 | |
| WO | WO 2006/004977 A2 * | 1/2006 | |
| WO | WO 2006/004979 A2 * | 1/2006 | |
| WO | WO 2006/020348 A2 * | 2/2006 | |
| WO | WO-2006/037055 A1 | 4/2006 | |
| WO | WO 2006/068662 A1 * | 6/2006 | |
| WO | WO-2007/068324 A1 | 6/2007 | |

OTHER PUBLICATIONS

ANON (R)-(−)-N-Methyl-3-(2-Methylphenoxy)Phenyl-3-Phenylpropylamine (S)-(+)-Mandelate Chemical Abstracts Service XP-002367856 Dec. 29, 2004.

Koenig, T.M. et al. "A Convenient Method for Preparing Enantiomerically Pure Norfluoxetine, Fluoxetine and Tomoxetine" Tetrahedron Letters, vol. 35, No. 0, pp. 1339-1342 (1994).

Strobel, H.A.; Heineman, W.R., Chemical Instrumentation: A Systematic Approach, 3rd dd. (Wiley & Sons: New York 1989)—pp. 391-393, 879-894, 922-925, 953.

Snyder, L.R.; Kirkland, J.J., Introduction to Modern Liquid Chromatography, 2nd ed. (John Wiley & Sons: New York 1979)—pp. 549-552, 571-572.

Srebnik, M. et al. "Chiral Synthesis via Organoboranes. 18. Selective Reductions. 43. Dissopinocampheylchloroborane as an Excellent . . ." J. Org. Chem. (1988), vol. 53, p. 2916-2920.

Sellers, J.A. et al. "Determination of the Enantiomer and Positional Isomer Impurities in Atomoxetine Hydrochloride with Liquid Chromatography Using Polysaccharide Chiral Stationary Phases." *J. of Pharmaceutical and Biomedical Analysis*, vol. 41, pp. 1088-1094 (2006).

Synthon BV, Research Disclosure, Atomoxetine hydrochloride polymoprhs, Nov. 2005.

Stephenson, Gregory A., et al., "Structural Determination of the Stable and Meta-Stable Forms of Atomoxetine HCl Using Single Crystal and Powder X-Ray Diffraction Methods", Journal of Pharmaceutical Sciences, Aug. 2006, vol. 95, No. 8, pp. 1677-1683.

Tomoxetine hydrochloride, 1998 JCPDS.

* cited by examiner

*Primary Examiner*—Brian J Davis
(74) *Attorney, Agent, or Firm*—Kenyon & Kenyon LLP

(57) ABSTRACT

Stable Atomoxetine hydrochloride, a process for the manufacture thereof, the use of stable Atomoxetine Hydrochloride for making a pharmaceutical formulation, a process for the preparation of any form of Atomoxetine Hydrochloride, and an analytical method for analyzing the stability of Atomoxetine Hydrochloride are provided.

26 Claims, No Drawings

STABLE ATOMOXETINE HYDROCHLORIDE, A PROCESS FOR THE PREPARATION THEREOF, AND AN ANALYTICAL CONTROL OF ITS STABILITY

CROSS-REFERENCE TO RELATED APPLICATIONS

This application claims the benefits of U.S. Provisional Patent Application No. 60/668,741, filed Apr. 5, 2005, U.S. Provisional Patent Application No. 60/686,386, filed May 31, 2005, and U.S. Provisional Patent Application No. 60/688,406, filed Jun. 7, 2005, the contents of all of which are incorporated herein by reference.

FIELD OF THE INVENTION

The present invention relates to stable Atomoxetine hydrochloride that is substantially free of impurities and degradation products, a process for the manufacture thereof, and an analytical method for predicting the stability of Atomoxetine Hydrochloride.

BACKGROUND OF THE INVENTION

Atomoxetine (ATM), known as (R)(−)-n-methyl-3-(2-methylphenoxy)-3-phenylpropylamine; has the following structure

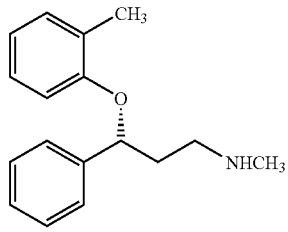

and a formula of $C_{17}H_{21}NO$, a molecular weight of 255.35, and a composition of 79.96 percent C, 8.29 percent H, 5.49 percent N, and 6.27 percent O, by weight. Atomoxetine is the (R)-(−) enantiomer of Tomoxetine. Atomoxetine is a competitive inhibitor of norepinephrine uptake in synaptosomes of rat hypothalamus. Atomoxetine is used for the treatment of Attention-Deficit-Hyperactivity Disorder (ADHD).

Atomoxetine HCl is marketed as STRATTERA®, which is prescribed as oral capsules having dosages of 10 mg, 18 mg, 25 mg, 40 mg, and 60 mg.

The stability of Atomoxetine Hydrochloride is known to be a serious problem. The synthesis of Atomoxetine Hydrochloride involves the use of excess of hydrogen chloride. The presence of free hydrogen chloride in excess can cause degradation in both the last steps of the manufacturing process and in storage. Therefore, for example, Sigma-Aldrich suggests storage at 2° to 8° C. (see: product number T7947, (R)-Tomoxetine HCl, www.signalaldrich.com), to avoid such degradation.

It is well known in the art that, for human administration, safety considerations require the establishment, by national and international regulatory authorities, of very low limits for identified, but toxicologically uncharacterized impurities, before an active pharmaceutical ingredient (API) product is commercialized. Typically, these limits are less than about 0.15 percent by weight of each impurity. Limits for unidentified and/or uncharacterized impurities are obviously lower. Therefore, in the manufacture of APIs, the purity of the products, such as Atomoxetine Hydrochloride, is required before commercialization, as is the purity of the active agent in the manufacture of formulated pharmaceuticals.

It is also known in the art that impurities in an API may arise from degradation of the API itself, which is related to the stability of the pure API during storage, and the manufacturing process, including the chemical synthesis. Process impurities include unreacted starting materials, chemical derivatives of impurities contained in starting materials, synthetic byproducts, and degradation products.

In addition to stability, which is a factor in the shelf life of the API, the purity of the API produced in the commercial manufacturing process is clearly a necessary condition for commercialization. Impurities introduced during commercial manufacturing processes must be limited to very small amounts, and are preferably substantially absent. For example, the ICH Q7A guidance for API manufacturers requires that process impurities be maintained below set limits by specifying the quality of raw materials, controlling process parameters, such as temperature, pressure, time, and stoichiometric ratios, and including purification steps, such as crystallization, distillation, and liquid-liquid extraction, in the manufacturing process. In the United States, the Food and Drug Administration guidelines recommend that the amounts of some impurities be limited to less than 0.1 percent.

As is known by those skilled in the art, the management of process impurities is greatly enhanced by understanding their chemical structures and synthetic pathways, and by identifying the parameters that influence the amount of impurities in the final product. Therefore, impurities in APIs result primarily from one of two sources, (I) the manufacturing process or synthesis of the API and (II) from the degradation of the API itself.

Once pure Atomoxetine Hydrochloride is obtained, i.e., the Atomoxetine Hydrochloride is substantially free of process impurities, or the process impurities are present in very small, limited amounts at the end of its manufacturing process. Degradation impurities (II), which are related to stability during storage, are the primary source of impurities, as long as contamination is prevented. Manufacturers are required by national and international laws and regulations to submit appropriate documentation to regulatory authorities, proving stability of both the APIs and formulated pharmaceuticals. It is therefore known in the art that stability of the API itself is a necessary condition for commercialization. See, e.g., ICH Q7A guidance for API manufacturers.

Generally, side products, by-products, and adjunct reagents (collectively "impurities") are identified spectroscopically and/or with another physical method, and then associated with a peak position, such as that in a chromatogram, or a spot on a TLC plate. (Strobel p. 953, Strobel, H. A.; Heineman, W. R., Chemical Instrumentation: A Systematic Approach, 3rd dd. (Wiley & Sons: New York 1989)). Thereafter, the impurity can be identified, e.g., by its relative position in the chromatogram, where the position in a chromatogram is conventionally measured in minutes between injection of the sample on the column and elution of the particular component through the detector. The relative position in the chromatogram is known as the "retention time."

As is known by those skilled in the art, the management of process impurities is greatly enhanced by understanding their chemical structures and synthetic pathways, and by identifying the parameters that influence the amount of impurities in the final product.

Therefore, an Atomoxetine Hydrochloride having improved stability would be advantageous. The present invention provides such an Atomoxetine Hydrochloride.

SUMMARY OF THE INVENTION

In one aspect, the present invention provides stable Atomoxetine Hydrochloride. The stable Atomoxetine Hydrochloride of the present invention contains a reduced amount of free hydrogen chloride, such that an aqueous solution of the stable Atomoxetine Hydrochloride has a pH of at least about 4. Preferably, the stable Atomoxetine Hydrochloride has a pH of from about 4 to about 7.

In another aspect, the present invention provides a process for preparing stable Atomoxetine Hydrochloride.

In yet another aspect, the present invention provides a method for analyzing Atomoxetine Hydrochloride stability, comprising determining the pH of a sample of Atomoxetine Hydrochloride in aqueous solution.

In one aspect, the present invention provides a method for analyzing Atomoxetine Hydrochloride stability, comprising determining the chloride content in Atomoxetine Hydrochloride.

In another aspect, the present invention provides a process for preparing a pharmaceutical formulation comprising stable Atomoxetine Hydrochloride comprising the steps of:

a) obtaining one or more samples of one or more Atomoxetine Hydrochloride batches;

b) measuring the level of any one of impurities:

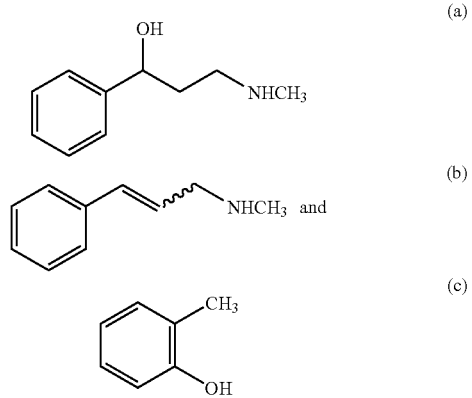

in each of the samples of step a);

c) selecting the Atomoxetine Hydrochloride batch that comprises a level of impurities impurity (a) of less than about 0.15% w/w, and a level of any one of impurities (b) and (c) of less than a about 0.10% w/w by HPLC, based on the measurement or measurements conducted in step b); and d) using the batch selected in step c) to prepare a pharmaceutical formulation comprising stable Atomoxetine Hydrochloride.

In yet another aspect, the present invention provides a process for preparing a crystalline or amorphous form of Atomoxetine Hydrochloride comprising the steps of:

a) obtaining one or more samples of one or more Atomoxetine Hydrochloride batches;

b) measuring the level of any one of impurities (a), (b) and (c) in each of the samples of step a);

c) selecting the Atomoxetine Hydrochloride batch that comprises a level of impurities impurity (a) of less than 0.15% w/w, and a level of any one of impurities (b) and (c) of less than a about 0.10% w/w by HPLC, based on the measurement or measurements conducted in step b); and d) using the batch selected in step c) to prepare said crystalline or amorphous form of Atomoxetine Hydrochloride.

In one aspect, the present invention provides an HPLC method for assaying any one of impurities (a), (b) or (c) of Atomoxetine Hydrochloride comprising the steps of:

a) combining a sample containing 1 mg of Atomoxetine Hydrochloride in 1 ml of a mixture of Phosphate buffer with PH of about 3/Acetonitrile (60/40);

b) injecting the mixture of step a) into a 250 mm×4.6 mm×5.0 μm YMC-Pack ODS-AQ (or similar) column;

c) gradually eluting the sample from the column using a mixture of Acetonitrile:Water (90:10) as an eluent and a buffer containing an aqueous solution of $NaH_2PO_4$ monohydrate in a concentration of about 2.8 mg/ml and 85% (w/w) $H_3PO_4$ to adjust a pH of about 3; and d) measuring any one of impurities (a), (b) and (c) content in the sample with a UV detector.

In another aspect, the present invention provides pharmaceutical formulations comprising the stable Atomoxetine Hydrochloride of the present invention, and a pharmaceutically acceptable excipient.

In yet another aspect, the present invention provides a process for preparing a pharmaceutical formulation comprising combining stable Atomoxetine Hydrochloride of the present invention with at least one pharmaceutically acceptable excipient.

In one aspect, the present invention provides the use of stable Atomoxetine Hydrochloride of the present invention for the manufacture of a pharmaceutical composition.

DETAILED DESCRIPTION OF THE INVENTION

As used herein, the term "free hydrogen chloride" refers to hydrogen chloride molecules that are not bound to Atomoxetine, such that the hydrogen chloride is present in an amount exceeding a 1:1 molar ratio with the Atomoxetine base in Atomoxetine Hydrochloride.

As used herein, the term "high vacuum" refers to a pressure of about 0 mm Hg to about 50 mm Hg.

As used herein, the term "low temperature" refers to a temperature of below 40° C., and, more preferably, to a temperature of below 30° C.

The three main impurities that result from the degradation of Atomoxetine Hydrochloride in presence of free HCl are:

Impurity (a): N-methyl-3-hydroxy-3-phenylpropylamine, which has the following structure

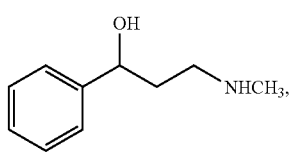

is a starting material in the synthesis of Atomoxetine, and is detected and resolved from Atomoxetine by HPLC with an RRt of 0.2;

Impurity (b): N-methyl-3-phenyl-2,3-propenylamine, which has the following structure

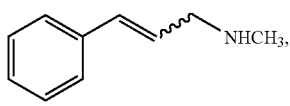

and is detected and resolved from Atomoxetine by HPLC with an RRt of 0.4; and

Impurity (c): ortho-Cresol (2-methylphenol), which has the following structure

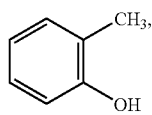

and is detected and resolved from Atomoxetine by HPLC with an RRt of 0.9.

As used herein, the term "stable", in reference to Atomoxetine Hydrochloride, refers to Atomoxetine Hydrochloride in which either the level of impurity (a) does not increase to more than about 0.15% w/w, or the levels of impurities (b) or (c) do not increase to more than 0.10% w/w, upon storage for at least about 58 hours at about 70° C.

The present invention provides stable Atomoxetine Hydrochloride.

The stable Atomoxetine Hydrochloride of the present invention contains a reduced amount of free hydrogen chloride, such that an aqueous solution of the stable Atomoxetine Hydrochloride has a pH of at least about 4. Preferably, the stable Atomoxetine Hydrochloride has a pH of from about 4 to about 7.

One method for preparing stable Atomoxetine Hydrochloride comprises removing any excess of free hydrogen chloride from the isolated crude Atomoxetine Hydrochloride product by high vacuum at low temperature. Removal by vacuum requires high vacuum pumps and neutralization of acidic hydrogen chloride vapours. Moreover, due to the high level of metal corrosion by hydrochloric acid, anhydrous evaporation conditions are required to avoid damage to stainless steel industrial vacuum equipment.

The present invention provides a process for preparing stable Atomoxetine Hydrochloride comrising removing any excess of free hydrogen chloride from the Atomoxetine Hydrochloride product by slurrying and/or washing with at least one solvent selected from a group consisting of water, a $C_3$ to $C_8$ ketone, and a $C_3$ to $C_8$ alcohol. The removal of hydrogen chloride by slurrying and/or washing with solvents is highly applicable to any industrial process for the synthesis of stable Atomoxetine Hydrochloride. Such a process is most effective when the washing and/or slurrying solvent dissolves hydrogen chloride and does not dissolve Atomoxetine Hydrochloride. Preferably, the $C_3$ to $C_8$ ketone is $C_3$ to $C_5$ ketone. More preferably, the $C_3$ to $C_5$ ketone is selected from the group consisting of acetone, methylethylketone. Most preferably, the $C_3$ to $C_5$ ketone is acetone. Preferably, the $C_3$ to $C_8$ alcohol is $C_3$ to $C_5$ alcohol. More preferably, the $C_3$ to $C_5$ alcohol is selected from the group consisting of propanol, isopropanol, and butanol. Most preferably, the $C_3$ to $C_5$ alcohol is butanol.

When slurry is used, the recovery comprises filtering the slurry, washing and drying. Preferably, the washing is with the solvent used for slurrying. Preferably, when slurrying with water, the temperature is of about 0° C. to about 10° C.

Preferably, when $C_3$ to $C_8$ ketone and $C_3$ to $C_8$ alcohol are used for the washing the temperature is of about 10° C. to about 30° C. Preferably, when water is used for the washing the temperature is of about 0° C. to about 30° C. Preferably, when acetone is used for the washing the temperature is of about 30° C. Preferably, the wet Atomoxetine Hydrochloride is further dried. Preferably, the drying is under vacuum at a temperature of about 60° C. to about 70° C.

As will be recognized by those skilled in the art, water provides great economical and environmental advantages over chemical solvents.

Stressed thermal stability tests demonstrate that a highly stable Atomoxetine Hydrochloride, is obtained when free HCl is absent or the pH is of more than about 4.0 in either dry or wet Atomoxetine Hydrochloride. However, the presence of free HCl in Atomoxetine Hydrochloride, which is easily detected by a pH test of a solution of Atomoxetine Hydrochloride in water, results in significant degradation of the Atomoxetine Hydrochloride, as described below.

Atomoxetine Hydrochloride samples analytical features:

|  | pH of 2% (w/V) aqueous solution | estimated free HCl content (w %) | water content (w %) |
|---|---|---|---|
| Sample 1 | 2.4 | 2% | 10% |
| Sample 2 | 5.8 | 0% | 11% |
| Sample 3 | 6.0 | 0% | 0.5% |
| Sample 4 | 5.9 | 0% | 0.0% |

Atomoxetine Hydrochloride samples stability test (70° C. for 58 hours) results

|  | Impurity (a) (HPLC A %) | Impurity (b) (HPLC A %) | Impurity (c) (HPLC A %) |
|---|---|---|---|
| Time zero |  |  |  |
| Sample 1 | not detected | not detected | not detected |
| Sample 2 | not detected | not detected | not detected |
| Sample 3 | not detected | not detected | not detected |
| Sample 4 | not detected | not detected | not detected |
| End of test time |  |  |  |
| Sample 1 | 10.5% | 14.2% | 26.2% |
| Sample 2 | not detected | not detected | not detected |
| Sample 3 | not detected | not detected | not detected |
| Sample 4 | not detected | not detected | not detected |

Impurity (a): N-methyl-3-hydroxy-3-phenylpropylamine;
Impurity (b): N-methyl-3-phenyl-2,3-propenylamine; and
Impurity (c): ortho-Cresol (2-methylphenol)

Heating under vacuum is commonly used in commercial synthesis to remove solvents from wet solids. Two samples of wet Atomoxetine Hydrochloride, following filtration from a crystallization medium, e.g., n-Butyl acetate as the solvent and aqueous hydrogen chloride as the reactant, are found to comprise:

|  | Atomoxetine HCl | Water | n-Butyl acetate | Free HCl | pH (2% in $H_2O$) |
|---|---|---|---|---|---|
| Sample 5 | 80.44% | 9.7% | 8.25% | 1.61% | 2.4 |
| Sample 6 | 83.54% | 10.5% | 4.77% | 1.19% | 2.4 |

A simple pH aqueous solution test, giving a pH of less than 4, demonstrates the non-negligible presence of free HCl in Atomoxetine Hydrochloride. This is confirmed by combining a loss on drying, quantitative determination of the water content, and a quantitative determination of the chloride ion content.

It is experimentally demonstrated that drying wet Atomoxetine Hydrochloride containing >2% free HCl in a vacuum oven at 70° C. severely degrades the product purity (HPLC results, weight percent). These experimental results are in agreement with the previously described stability data.

| Sample 5 | Impurity (a) | Impurity (b) | Impurity (c) |
|---|---|---|---|
| Before drying | not detected | not detected | not detected |
| After drying | 0.31% | 0.04% | 0.12% |

At lower temperatures, e.g., 40° C., the stability of Atomoxetine Hydrochloride samples, having a water solution pH test of less than 4 are compromised, while Atomoxetine Hydrochloride samples, having a water solution pH test of greater than 4, are stable. Collected data are summarized below:

Atomoxetine Hydrochloride samples analytical features:

|  | aqueous pH test results | water content (w %) |
|---|---|---|
| Sample 7 | 2.4 | 9.0% |
| Sample 8 | 4.4 | 3.8% |
| Sample 9 | 4.8 | 3.6% |
| Sample 10 | 6.1 | 0.5% |

|  | Impurity (a) (HPLC A %) | Impurity (b) (HPLC A %) | Impurity (c) (HPLC A %) |
|---|---|---|---|
| Sample 7 stability test (40° C., five days) results: | | | |
| Time zero | 0.014% | not detected | 0.018% |
| End of test time | 0.633% | 0.0482% | 0.689% |
| Sample 8 stability test (40° C., five days) results: | | | |
| Time zero | not detected | not detected | not detected |
| End of test time | not detected | not detected | not detected |
| Sample 9 stability test (40° C., five days) results: | | | |
| Time zero | not detected | not detected | not detected |
| End of test time | not detected | not detected | not detected |
| Sample 10 stability test (40° C., five days) results: | | | |
| Time zero | not detected | not detected | not detected |
| End of test time | not detected | not detected | not detected |
| Sample 11 stability test (40° C., 75% RH) results: | | | |
| Time zero | 0.01 | not detected | not detected |
| 1 month | 0.02 | 0.006 | not detected |
| 2 months | 0.02 | 0.007 | not detected |
| 3 months | 0.02 | 0.003 | not detected |
| 6 month | 0.01 | not detected | not detected |

Moreover, dry Atomoxetine Hydrochloride undergoes degradation upon simple contact with HCl gas flow at room temperature, even during short exposure times, as described below:

|  | aqueous pH test result | water content (w %) |
|---|---|---|
| Before contact with HCl gas flow | | |
| (Sample 12) | 6.1 | 0.04% |
| After contact with HCl gas flow | | |
| (Sample 12) | 2.8 | 0.06% |

| Sample 12 HPLC A % results: | | | |
|---|---|---|---|
|  | Impurity (a) | Impurity (b) | Impurity (c) |
| Before contact with HCl gas flow | not detected | not detected | not detected |
| After contact with HCl gas flow | 0.10% | 0.032% | 1.54% |

Free hydrogen chloride in wet Atomoxetine Hydrochloride can be detected by a combination of quantitative analysis techniques, such as the determinations of: the chloride ion concentration, the total acid content, the water content, or the loss on drying.

The present invention provides a method for analyzing Atomoxetine Hydrochloride stability, comprising determining the pH of a sample of Atomoxetine Hydrochloride in aqueous solution. The process comprises dissolving Atomoxetine Hydrochloride in water at a temperature of about 20° C. to about 30° C. to obtain a solution and measuring the pH. Preferably, the dissolution of Atomoxetine Hydrochloride is accelerated by using a sonication. Preferably, the pH is measured with a glass electrode. The determination of the pH of Atomoxetine Hydrochloride in water has been found to be a very effective predictor of the stability of Atomoxetine Hydrochloride samples.

The present invention provides another method for analyzing Atomoxetine Hydrochloride stability, comprising determining the chloride content in Atomoxetine Hydrochloride. Preferably, the chloride determination is by titration with $AgNO_3$.

The present invention provides a process for preparing a pharmaceutical formulation comprising stable Atomoxetine Hydrochloride comprising the steps of:

a) obtaining one or more samples of one or more Atomoxetine Hydrochloride batches;

b) measuring the level of any one of impurities (a), (b) and (c) in each of the samples of step a);

c) selecting the Atomoxetine Hydrochloride batch that comprises a level of impurities impurity (a) of less than about 0.15% w/w, and a level of any one of impurities (b) and (c) of less than a about 0.10% w/w by HPLC, based on the measurement or measurements conducted in step b); and d) using the batch selected in step c) to prepare a pharmaceutical formulation comprising stable Atomoxetine Hydrochloride.

Preferably, the Atomoxetine Hydrochloride sample of step a) comprises a sufficiently low level of impurities (a), (b) and (c). More preferably, the Atomoxetine Hydrochloride sample of step a) contains less than about 0.15% w/w by HPLC of impurity (a), and less than about 0.10% w/w by HPLC of any one of impurities (b) and (c).

The present invention provides a process for preparing a crystalline or amorphous form of Atomoxetine Hydrochloride comprising the steps of:

a) obtaining one or more samples of one or more Atomoxetine Hydrochloride batches;

b) measuring the level of any one of impurities (a), (b) and (c) in each of the samples of step a);

c) selecting the Atomoxetine Hydrochloride batch that comprises a level of impurities impurity (a) of less than about 0.15% w/w, and a level of any one of impurities (b) and (c) of less than a about 0.10% w/w by HPLC, based on the measurement or measurements conducted in step b); and d) using the batch selected in step c) to prepare said crystalline or amorphous form of Atomoxetine Hydrochloride.

Preferably, the Atomoxetine Hydrochloride sample of step a) comprises a sufficiently low level of impurities (a), (b) and (c). More preferably, the Atomoxetine Hydrochloride sample of step a) contains less than about 0.15% w/w by HPLC of impurity (a), and less than about 0.10% w/w by HPLC of any one of impurities (b) and (c).

The present invention provides an HPLC method for assaying any one of impurities (a), (b) or (c) of Atomoxetine Hydrochloride comprising the steps of:

a) combining a sample containing 1 mg of Atomoxetine Hydrochloride in 1 ml of a mixture of Phosphate buffer with PH of about 3/Acetonitrile (60/40);

b) injecting the mixture of step a) into a 250 mm×4.6 mm×5.0 µm YMC-Pack ODS-AQ (or similar) column;

c) gradually eluting the sample from the column using a mixture of Acetonitrile:Water (90:10) as an eluent and a buffer containing an aqueous solution of $NaH_2PO_4$ monohydrate; and d) measuring any one of impurities (a), (b) and (c) content in the sample with a UV detector.

Preferably, the aqueous solution of $NaH_2PO_4$ monohydrate is in a concentration of about 2.8 mg/ml and 85% (w/w) $H_3PO_4$ to adjust a pH of about 3.

Preferably, the elution time in step c) is about 30 min.

Preferably, the UV wavelength is about 215 nm.

The present invention also encompasses pharmaceutical formulations comprising the stable Atomoxetine Hydrochloride of the present invention, and a pharmaceutically acceptable excipient.

The present invention further encompasses a process for preparing a pharmaceutical formulation comprising combining stable Atomoxetine Hydrochloride of the present invention with at least one pharmaceutically acceptable excipient.

The present invention further encompasses the use of stable Atomoxetine Hydrochloride of the present invention for the manufacture of a pharmaceutical composition.

Methods of administration of a pharmaceutical composition of the present invention can be administered in various preparations depending on the age, sex, and symptoms of the patient. The pharmaceutical compositions can be administered, for example, as tablets, pills, powders, liquids, suspensions, emulsions, granules, capsules, suppositories, injection preparations (solutions and suspensions), and the like.

Pharmaceutical compositions of the present invention can optionally be mixed with other forms of Atomoxetine Hydrochloride and/or other active ingredients. In addition, pharmaceutical compositions of the present invention can contain inactive ingredients such as diluents, carriers, fillers, bulking agents, binders, disintegrants, disintegration inhibitors, absorption accelerators, wetting agents, lubricants, glidants, surface active agents, flavoring agents, and the like.

Diluents increase the bulk of a solid pharmaceutical composition, and may make a pharmaceutical dosage form containing the composition easier for the patient and care giver to handle. Diluents for solid compositions include, for example, microcrystalline cellulose (e.g., AVICEL®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g., carbopol), carboxymethylcellulose sodium, dextrin, ethyl cellulose, gelatin, guar gum, hydrogenated vegetable oil, hydroxyethyl cellulose, hydroxypropyl cellulose (e.g., KLUCEL®), hydroxypropyl methyl cellulose (e.g., METHOCEL®), liquid glucose, magnesium aluminum silicate, maltodextrin, methylcellulose, polymethacrylates, povidone (e.g., KOLLIDON®, PLASDONE®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g., AC-DI-SOL®, PRIMELLOSE®), colloidal silicon dioxide, croscarmellose sodium, crospovidone (e.g., KOLLIDON®, POLYPLASDONE®), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB®) and starch.

Glidants can be added to improve the flowability of a non-compacted solid composition and to improve the accuracy of dosing. Excipients that may finction as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, stable Atomoxetine Hydrochloride and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol, and invert sugar may be added to improve the taste.

Preservatives and chelating agents such as alcohol, sodium benzoate, butylated hydroxy toluene, butylated hydroxyanisole, and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

When preparing injectable (parenteral) pharmaceutical compositions, solutions and suspensions are sterilized and are preferably made isotonic to blood. Injection preparations may use carriers commonly known in the art. For example, carriers for injectable preparations include, but are not limited to, water, ethyl alcohol, propylene glycol, ethoxylated isostearyl alcohol, polyoxylated isostearyl alcohol, and fatty acid esters of polyoxyethylene sorbitan. One of ordinary skill in the art can easily determine with little or no experimentation the amount of sodium chloride, glucose, or glycerin necessary to make the injectable preparation isotonic. Additional ingredients, such as dissolving agents, buffer agents, and analgesic agents may be added.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages can be conveniently presented in unit dosage form and prepared by any of the methods well-known in the pharmaceutical arts.

ANALYTICAL METHODS

Determination of pH of Atomoxetine Hydrochloride Samples in Aqueous Solution

A 2 g sample of Atomoxetine Hydrochloride is dissolved in 100 ml of deionized water at temperature between about 20° C. and about 30° C. with sonication if required to obtain a complete solution. The pH is measured with a glass electrode at temperature of between about 20° C. and about 30° C.

Chloride Determination in Atomoxetine Hydrochloride by Titration

A 250 mg sample of Atomoxetine Hydrochloride is weighed accurately, dissolved in 50 ml of deionized water, and 5 ml of a 4 percent w/v solution of $HNO_3$ are added. The obtained mixture is titrated potentiometrically with 0.1N $AgNO_3$.

Calculation:

$$\% \text{ Chloride} = \frac{V \text{ ml}_{titrant} \times 0.1 \times F_{titrant} \times 35.45}{\text{sample weight(mg)}} \times 100$$

Wherein V is the titrant volume and F is titrant correction factor.

| HPLC analysis | |
| --- | --- |
| Column & Packing: | YMC-Pack ODS-AQ, S-5 µm, 12 nm 250 mm × 4.6 mm × 5.0 µm, cat n.042574458 (W) or equivalent |

-continued

HPLC analysis

| | |
|---|---|
| Buffer: | $NaH_2PO_4$ monohydrate pH 3.0:2.8 g in 1000 ml of deionized water, adjust pH at 3.0 with $H_3PO_4$ 85% (w/w). Filter on a 0.45 μm filter. |
| Eluent A: | Acetonitrile:Water 90:10 |

| Gradient | Time (min) | % Buffer | % Eluent A |
|---|---|---|---|
| | 0 | 85 | 15 |
| | 20 | 48 | 52 |
| | 30 | 48 | 52 |
| Equilibrium time: | 8 minutes | | |
| Flow Rate: | 1.5 ml/min | | |
| Detector: | UV at 215 nm | | |
| Column temperature: | 40° C. | | |
| Diluent | Buffer:Acetonitrile (60:40) | | |
| Injection | 5 μl | | |

Typical relative retention times are:

| | |
|---|---|
| Impurity (a): N-methyl-3-hydroxy-3-phenylpropylamine | RRt = 0.2; |
| Impurity (b): N-methyl-3-phenyl-2,3-propenylamine | RRt = 0.4; |
| Impurity (c): ortho-Cresol (2-methylphenol) | RRt = 0.9; and |
| Atomoxetine Hydrochloride | RRt = 1.0. |

EXAMPLES

Example 1

Preparation of Atomoxetine Hydrochloride

Under stirring, while maintaining the temperature between about 22° C. and about 25° C. with a water bath, 286 g (2.825 mol) of aqueous hydrogen chloride (36%) are dropped on 5063 g (2.379 mol) of Atomoxetine base in a solution of n-butyl acetate, prepared as described in U.S. Provisional Applications Nos. 60/583643, 60/583644, and 60/622065. The hydrochloride crystallized. The resulting suspension is stirred at about 25° C. for about one hour, and the solid is collected by filtration, and washed three times with 900 ml of n-butyl acetate. About 850 g of wet Atomoxetine Hydrochloride are obtained. After two separate preparations, samples of obtained wet solids are dissolved in water (2 g in 100 ml). The pH determined for each sample is 2.39 and pH 2.40, respectively.

Example 2

Removal of Free HCl by Water Slurry

About 100 g of wet product, having an estimated Atomoxetine Hydrochloride content of 83.5 g, based on loss on drying, prepared as described in example 1, are mixed with 100 ml of water at 5° C. for 30 minutes to form a slurry, collected by filtration, and washed with 30 ml of water (a 200 mg sample is dissolved in 10 ml of water, and is found to have a pH of 4.4).

The wet solid is mixed with 100 ml of water at 5° C. for 30 minutes a second time, collected by filtration and washed with 30 ml of water. 90.1 g of wet Atomoxetine Hydrochloride are obtained (a 2 g sample is dissolved in 100 ml of water, and is found to have a pH of 5.9). The wet product is dried in vacuo at about 60° to about 70° C., providing 79.9 g of dry Atomoxetine Hydrochloride, a yield of 95.7%. Purity: >99.8%.

Example 3

Removal of Free HCl by Acetone Washing 70 g of wet Atomoxetine Hydrochloride, prepared as described in example 1, are washed twice with 62.5 ml of acetone on a Buchner funnel at room temperature, i.e., about 20° to about 25° C. About 65 g of wet Atomoxetine Hydrochloride are obtained. The wet product is dried in vacuo at 65° C., giving 62.4 g of dry Atomoxetine Hydrochloride, a yield of about 94 percent. A sample is dissolved in water in a concentration of about 2 percent w/V, and a pH of 4.6 is determined. Purity: >99.8%.

What is claimed:

1. Stable Atomoxetine Hydrochloride.
2. The stable Atomoxetine Hydrochloride of claim 1, wherein an aqueous solution of the Atomoxetine Hydrochloride has a pH of at least about 4.
3. The stable Atomoxetine Hydrochloride of claim 2, wherein the aqueous solution of the Atomoxetine Hydrochloride has a pH of from about 4 to about 7.
4. A process for preparing stable Atomoxetine Hydrochloride, comprising slurrying and/or washing Atomoxetine Hydrochloride containing an excess of hydrogen chloride with at least one solvent selected from a group consisting of water, a $C_3$ to $C_8$ ketone, and a $C_3$ to $C_8$ alcohol.
5. The process of claim 4, wherein the $C_3$ to $C_8$ ketone is a $C_3$ to $C_5$ ketone.
6. The process of claim 5, wherein the $C_3$ to $C_5$ ketone is selected from the group consisting of acetone and methylethylketone.
7. The process of claim 6, wherein the $C_3$ to $C_5$ ketone is acetone.
8. The process of claim 4, wherein the $C_3$ to $C_8$ alcohol is a $C_3$ to $C_5$ alcohol.
9. The process of claim 8, wherein the $C_3$ to $C_5$ alcohol is selected from the group consisting of propanol, isopropanol, and butanol.
10. The process of claim 9, wherein the $C_3$ to $C_5$ alcohol is butanol.
11. The process of claim 4, wherein the solvent is water.
12. The process of claim 4, wherein Atomoxetine Hydrochloride is slurried in the solvent.
13. The process of claim 12, further comprising recovering the stable Atomoxetine Hydrochloride by filtering, washing, and drying the slurried Atomoxetine Hydrochloride.
14. The process of claim 12, wherein the Atomoxetine Hydrochloride is washed with the solvent used for slurrying.
15. The process of claim 12, wherein the solvent is water.
16. The process of claim 15, wherein the Atomoxetine Hydrochloride is slurried at a temperature of about 0° C. to about 10° C.
17. The process of claim 4, wherein the washing is with a $C_3$ to $C_8$ ketone and a $C_3$ to $C_8$ alcohol.
18. The process of claim 17, wherein the Atomoxetine Hydrochloride is washed at a temperature is of about 10° C. to about 30° C.
19. The process of claim 4, wherein the Atomoxetine Hydrochloride is washed with water.
20. The process of claim 19, wherein the Atomoxetine Hydrochloride is washed at a temperature of about 0° C. to about 30° C.

21. The process of claim 4, wherein the Atomoxetine Hydrochloride is washed with acetone.

22. The process of claim 21, wherein the Atomoxetine Hydrochloride is washed at a temperature of about 30° C.

23. The process of claim 4, further comprising drying the washed Atomoxetine Hydrochloride.

24. The process of claim 23, wherein the Atomoxetine Hydrochloride is dried under vacuum at a temperature of about 60° C. to about 70° C.

25. A pharmaceutical formulation comprising a stable Atomoxetine Hydrochloride and a pharmaceutically acceptable excipient.

26. A process for preparing a pharmaceutical formulation, the process comprising combining a stable Atomoxetine Hydrochloride with at least one pharmaceutically acceptable excipient.

* * * * *

UNITED STATES PATENT AND TRADEMARK OFFICE
CERTIFICATE OF CORRECTION

PATENT NO. : 7,569,729 B2  Page 1 of 1
APPLICATION NO. : 11/399055
DATED : August 4, 2009
INVENTOR(S) : Castelli et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 184 days.

Signed and Sealed this

Seventh Day of September, 2010

David J. Kappos
*Director of the United States Patent and Trademark Office*